(12) United States Patent
Stancanello (10) Patent No.: US 9,403,034 B2
(45) Date of Patent: Aug. 2, 2016

(54) TIME-RESOLVED TOMOSYNTHESIS IMAGING

(71) Applicant: Joseph Stancanello, Gif sur Yvette (FR)

(72) Inventor: Joseph Stancanello, Gif sur Yvette (FR)

(73) Assignee: Siemens Aktiengesellschaft, München (SE)

( * ) Notice: Subject to any disclaimer, the term of this patent is extended or adjusted under 35 U.S.C. 154(b) by 348 days.

(21) Appl. No.: 13/632,239

(22) Filed: Oct. 1, 2012

(65) Prior Publication Data

US 2013/0083889 A1 Apr. 4, 2013

(30) Foreign Application Priority Data

Sep. 30, 2011 (DE) .......................... 10 2011 083 854

(51) Int. Cl.
 *A61B 5/103* (2006.01)
 *A61B 6/02* (2006.01)
 *A61N 5/10* (2006.01)
 *A61B 6/00* (2006.01)

(52) U.S. Cl.
 CPC .............. *A61N 5/1037* (2013.01); *A61B 6/025* (2013.01); *A61B 6/486* (2013.01); *A61B 6/488* (2013.01); *A61B 6/5288* (2013.01); *A61N 2005/1061* (2013.01)

(58) Field of Classification Search
 CPC .......... A61B 6/025; A61B 6/027; A61B 6/03; A61B 6/032; A61B 6/48; A61B 6/486; A61B 6/503; A61B 6/504; A61B 6/5234; A61B 6/5288; A61B 6/541; A61B 6/542
 USPC ........................................... 378/8, 15, 19, 23
 See application file for complete search history.

(56) References Cited

U.S. PATENT DOCUMENTS

| | | | |
|---|---|---|---|
| 2005/0201509 A1* | 9/2005 | Mostafavi | A61B 5/1135 378/8 |
| 2007/0286331 A1* | 12/2007 | Keall et al. | 378/8 |
| 2010/0290586 A1 | 11/2010 | Friedrich | |
| 2011/0075809 A1 | 3/2011 | Boese et al. | |
| 2011/0211665 A1* | 9/2011 | Maurer et al. | 378/9 |
| 2012/0039433 A1* | 2/2012 | Berkus | A61B 5/113 378/8 |

FOREIGN PATENT DOCUMENTS

| | | |
|---|---|---|
| DE | 10 2009 021 740 A1 | 11/2010 |
| DE | 10 2009 043 420 A1 | 4/2011 |

OTHER PUBLICATIONS

German Office Action dated Dec. 6, 2012 for corresponding German Patent Application No. DE 10 2011 083 854.6 with English translation.

(Continued)

*Primary Examiner* — Robert Kim
*Assistant Examiner* — Eliza Osenbaugh-Stewar
(74) *Attorney, Agent, or Firm* — Lempia Summerfield Katz LLC (57) ABSTRACT

A method for time-resolved tomosynthesis imaging for a moving object includes moving an imaging device having an x-ray source and an x-ray detector around the moving object and recording raw image data for a temporal series of tomosynthesis images. The method also includes reconstructing the temporal series of tomosynthesis images from the raw image data. While the imaging device is being moved, a motion speed of the imaging device is matched to a speed, at which the moving object is moving.

21 Claims, 4 Drawing Sheets

(56) References Cited

OTHER PUBLICATIONS

D. R. Simpson et al., "A Survey of Image-Guided Radiation Therapy Use in the United States," Cancer, vol. 116(16), pp. 1-8, Aug. 15, 2010.

K. M. Karlsson et al., "Dedicated magnetic resonance imaging in the radiotherapy clinic," Abstract, Int J. Radiat Oncol Biol Phys, vol. 74(2), Jun. 1, 2009.

D. Verellen et al., "Gating and tracking, 4D in thoracic tumors," Cancer Radiotherapy (14), pp. 446-454, Oct. 2010.

G Li et al., "Advances in 4D Medical Imaging and 4D Radiation Therapy," Technology in Cancer Research and Treatment, vol. 7(1), pp. 67-81, Feb. 2008.

J. Lu et al., "Four-dimensional cone beam CT with adaptive gantry rotation and adaptive data sampling," Med Phys. 34(9), pp. 3520-3529, Sep. 2007.

Chinese Office Action for related Chinese Application No. 201210355645.8, mailed Apr. 3, 2015, with English Translation.

* cited by examiner

TIME-RESOLVED TOMOSYNTHESIS IMAGING

This application claims the benefit of DE 10 2011 083 854.6, filed on Sep. 30, 2011.

BACKGROUND

The present embodiments relate to a method for time-resolved tomosynthesis imaging, by which a moving object may be imaged.

Radiation therapy is an established method, in which ionizing radiation is employed for treating pathological tissue such as, for example, tumor tissue. The aim of radiation therapy is to irradiate the tissue requiring treatment with a sufficient therapeutic dose while at the same time sparing surrounding healthy tissue. The therapeutic effect is based on ionizing radiation affecting healthy and pathological tissue differently.

Safety margins, by which the target volume is enlarged, may be employed to provide that uncertainties that, for various reasons, may occur between a planning and treatment phase in the positioning of the tissue requiring treatment will not jeopardize the treatment's success.

Image-guided radiation therapy (IGRT) enables the uncertainties in irradiating the target volume to be reduced. IGRT allows the visualization of the target volume, organs at risk (OAR), and surrounding healthy tissue before irradiating commences in order to irradiate the target volume more accurately and employ smaller safety margins.

Various imaging modalities have been proposed for IGRT. Imaging methods that take account of the motion/deformation resulting from, for example, breathing movement may also be employed for IGRT. Various four-dimensional (4D) approaches may be applied. The approaches may already be applied during the planning phase for more accurately identifying the target volume and organs at risk, but the approaches may also be applied immediately before an irradiating phase for identifying the limits of motion of the target volume and organs at risk.

SUMMARY AND DESCRIPTION

The present embodiments may obviate one or more of the drawbacks or limitations in the related art. For example, a method for imaging a moving object that accurately images internal structures of the moving object and places less of a demand on the mechanical capability of the imaging device is provided.

One embodiment of a method for time-resolved tomosynthesis imaging for a moving object includes moving an imaging device having an x-ray source and an x-ray detector around the moving organ and recording raw image data for a temporal series of tomosynthesis images. The method also includes reconstructing the temporal series of tomosynthesis images from the raw image data.

While the imaging device is being moved (e.g., while the imaging device is being rotated in its entirety around a center of rotation through 360°), a motion speed of the imaging device may be matched to a speed, at which the moving object is moving.

A method of such kind allows time-resolved tomographic imaging, even when the imaging device is limited in terms of the speed, at which the x-ray source and x-ray detector move. For that limitation, four-dimensional image-recording methods may, for example. In such case, the recording time is short compared to the breathing cycle. For example, a currently available CT scanner may execute a complete rotation in only 0.33 s, which is negligibly short compared with the 4 to 6 s that a physiological breathing cycle takes. A CT scanner having such capabilities is, however, costly to construct.

Imaging devices having a rotation time that is significantly longer may be constructed more easily and economically. An object's movement (e.g., a breathing movement) may affect the image quality. This may be the case when, for example, a CT scanner is rotated so slowly that the duration of a complete rotation corresponds approximately to the period of the breathing cycle. Even a cone-beam CT scanner that is mounted on a linear accelerator (LINAC) of the radiation-therapy device uses up to 60 s to perform one complete rotation.

It may, for example, be advantageous to employ CT scanners for digital tomosynthesis. In such a case, only the image data from a limited angle range is used for reconstructing. The target volume may be shown in a time-resolved manner in the case of a slowly rotating CT scanner. In such a case, the complete rotation takes approximately 4 to 6 s. For example, a breathing movement may be reproduced in the temporal series of tomosynthesis images.

The motion of the CT scanner may, for example, be synchronized with a quasi-cyclic movement of the target volume (e.g., breathing movement) such that a complete rotation of the CT scanner roughly concurs (e.g., correlates) with the movement period (e.g., the duration of one breathing cycle of the breathing movement; approximately 4 to 6 s).

An angle range of 40° may be covered in 0.67 s, or an angle range of 60° may be covered in 1 s if a complete 360° rotation is performed in 6 s. The angle range enables a sufficient number of individual items of projection image data to be recorded for reconstructing a digital tomosynthesis corresponding to a breathing phase having a duration of 0.67 to 1 s. The entire breathing cycle may accordingly be represented in a time-resolved manner by a data record of individual digital tomosynthesis images assigned to the 6 (or more) breathing phases.

In an embodiment, the object may move at a varying speed while the raw image data is being recorded, and the motion speed of the imaging device may be matched to the varying speed of the object. The matching may be performed within one movement cycle.

The speed of the gantry may be matched to the steepness of the phase. Thus, for example, the inhalation phase is steeper than the exhalation phase so that an equal number of projection images for a predefined angle range are to be recorded in a shorter time in the inhalation phase compared with the exhalation phase. As a surrogate for the breathing phase, using which surrogate the steepness may be determined, a signal coming from an external sensor (e.g., an optical system that records the patient's surface, or from a breathing belt) may be used.

A breathing signal may be recorded during the controlling process, and a pre-estimated breathing signal may be determined from the breathing signal. The pre-estimated breathing signal may be used for controlling the motion speed of the imaging device.

The imaging device may, for example, be moved around the object such that the motion of the x-ray source and the x-ray detector is in a single plane, with the imaging device being moved around the object, for example, through 360°. The method may be applied also in the case of conventional CT scanners having a two-dimensional x-ray detector or in the case of a cone-beam CT scanner such as may be integrated in, for example, a radiation-therapy device.

In one embodiment, the imaging device is moved such that the angle range, from which the raw image data for reconstructing an individual image in the temporal series of tomosynthesis images is recorded, is covered in less than 2 seconds (e.g., in less than 1.5 seconds or less than 1 second). Typical breathing movements may in that way be represented in a time-resolved manner with a high degree of accuracy.

In one embodiment, the angle range, from which the raw image data for reconstructing an individual image in the temporal series is recorded, may be 35° to 100° (e.g., 40° to 70°).

The imaging device may be moved long enough for at least 4 phases (e.g., at least 6 phases) of the movement of the object to be imaged in the temporal series of the tomosynthesis images.

The raw image data may be recorded such that the reconstructed individual images in the temporal series have different tomosynthesis reconstruction levels.

The tomosynthesis reconstruction levels of two successive individual images in the temporal series of the tomosynthesis images may, for example, have a mutual angle of at least 20° or 30° (e.g., at least 40° and at most, at least 50°). An embodiment of such kind is easy to implement using a rotating gantry.

In a development of the method, the temporal series of the tomosynthesis images may be used in preparation for a radiation-therapy session and/or during a radiation-therapy session. This will enable a volumetric 4D IGRT to be implemented in a relatively simple manner.

The imaging method may be suitable for radiation therapy. Radiation-therapy devices may have an integrated x-ray-imaging device having an x-ray source and a two-dimensional x-ray detector. Those imaging devices may not, however, be moved as flexibly as a free-standing imaging device because the imaging devices are mechanically coupled to other components of the radiation-therapy device.

A precise and time-resolved representation of the target volume may be achieved using the present imaging method. The present imaging method may be used, for example, to image a quasi-cyclic movement of the target volume. An example of a typical quasi-cyclic movement of a target volume in radiation therapy is a movement of the target volume due to breathing.

This has the advantage that safety margins may be reduced because the location of the target volume may be determined more accurately. The fact that it may be problematic to employ safety margins is countered because there will be an inverse correlation between the size of the target volume and the dose that may be applied when the surrounding healthy tissue is to be simultaneously spared.

Various techniques are able to compensate possible movements/deformations of the anatomy of the patient. For example, a combination of all possible locations of the target volume during different movement phases (known also as the internal target volume (ITV)) may be formed, and 3D optimizing may be matched accordingly.

The target volume may be identified in one movement phase, and the contour of the target volume may be transferred to the other movement phases in order to carry out four-dimensional optimizing. A thus optimized or matched irradiating plan may be used for implementing tracking-therapy methods.

Another possible irradiating method is based on the gating method. In the gating method, a specific movement phase is used for planning and then performing the irradiation. The imaging method may also be employed in the case of a method of such kind for identifying what movement phase the target volume is in.

One embodiment of an imaging device includes an x-ray source and x-ray detector. The imaging device also includes a control device for controlling movement of the imaging device and for controlling the x-ray source and x-ray detector for recording raw image data. The imaging device includes a reconstruction device for reconstructing a temporal series of tomosynthesis images from the raw image data.

The control device may be embodied such that when the raw image data is being recorded, a motion speed of the imaging device is matched to a speed, at which the moving object is moving.

The imaging device may, by appropriately configuring the control device and/or reconstruction device, be embodied such that one of the above-described methods is performed when the imaging device is operated.

The imaging device may be integrated in a radiation-therapy device such that a therapeutic radiation source is also moved when the imaging device is moved. This embodiment of a radiation-therapy device has the disadvantage that relatively slow rotation speeds may be achieved compared with pure computerized tomography. Accurate and time-resolved quasi three-dimensional imaging (e.g., tomosynthesis imaging) may also be achieved using a device of such kind.

The foregoing and following description of the individual features, advantages, and effects each relate both to the device-specific and method-specific category without being explicitly mentioned in each case. The individual features disclosed therein may also be in combinations other than those shown.

DETAILED DESCRIPTION OF THE DRAWINGS

Figure 1:
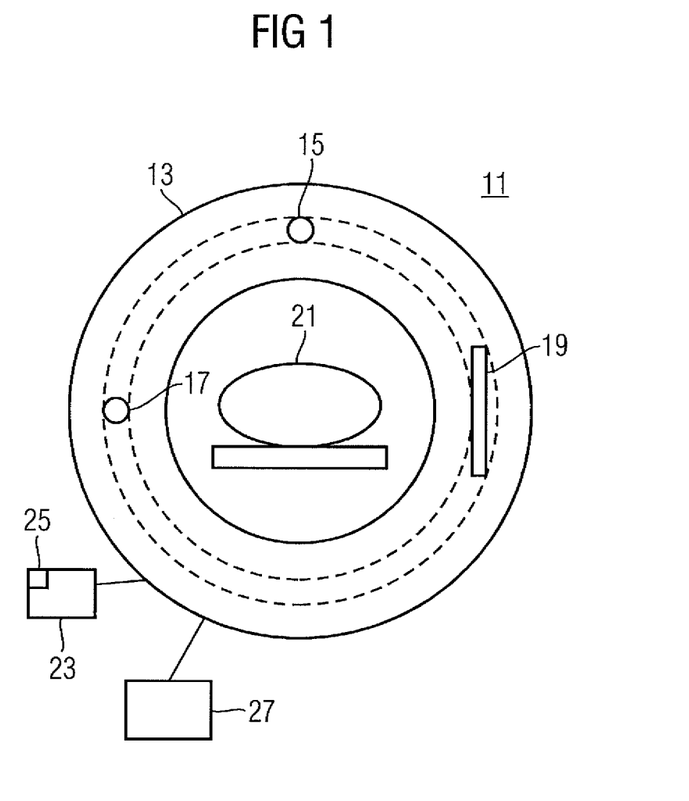
FIG. 1 shows a structure of a radiation-therapy device having an o-shaped gantry.

FIG. 1 shows a radiation-therapy device 11 having an o-shaped gantry 13. A therapeutic radiation source 15 is mounted capable of rotating in the gantry 13. The same structural arrangement, in which the therapeutic radiation source 15 is mounted capable of rotating, supports a diagnostic x-ray source 17 and a diagnostic, two-dimensional x-ray detector 19 (e.g., an imaging device). Image data of a patient 21 positioned in the center may be recorded using the imaging device.

Rotating of the imaging device 17, 19 and recording of the image data are controlled by a control device 23 belonging to the radiation-therapy device 11. The raw image data is processed in a reconstruction device 27 that reconstructs digital tomosynthesis images from the raw image data.

Control device 23 has an input, via which a signal characterizing the motion of the object to be imaged in patient 21 may be fed to control device 23. The control device 23 is able to change the rotation speed of imaging device 17, 19 during a movement cycle and match the rotation speed to a speed, at which the object to be imaged is moving.

The control device 23 may, for example, determine the steepness of a surrogate signal characterizing the motion of the object and accordingly set the speed of rotation of imaging device 17, 19 differently in different movement phases. The imaging device 17, 19 may be moved faster during movement phases, in which the surrogate signal exhibits greater steepness, than in movement phases, in which the surrogate signal exhibits lesser steepness.

Figure 2:
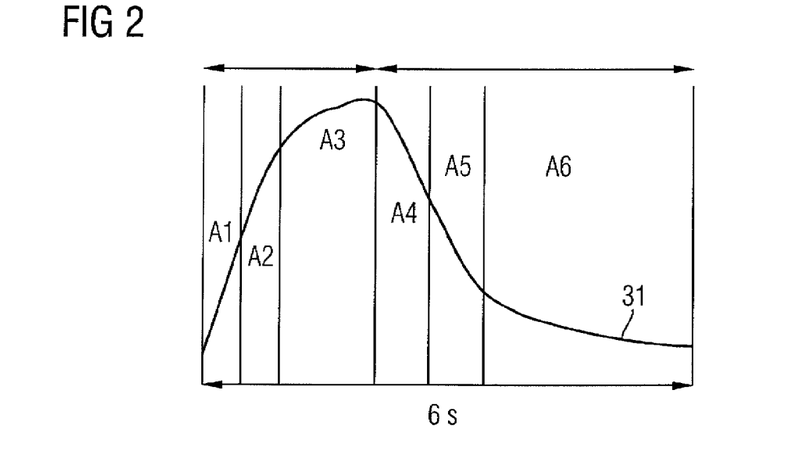
FIG. 2 shows a movement signal of a breathing cycle.

Shown in FIG. 2 is surrogate signal 31 for one breathing cycle. The individual breathing phases (e.g., early, mid, and late inhalation: A1, A2, A3; early, mid, and late exhalation: A4, A5, A6) are shown superimposed on surrogate signal 31. The late exhalation phase A6 lasts significantly longer than, for example, early the inhalation phase A1.

An angle range covered during the late exhalation A6 for recording the raw tomosynthesis image data may accordingly be traveled through at a significantly slower motion speed for the imaging device 17, 19 than the angle range assigned to the early inhalation A1.

Figure 3:
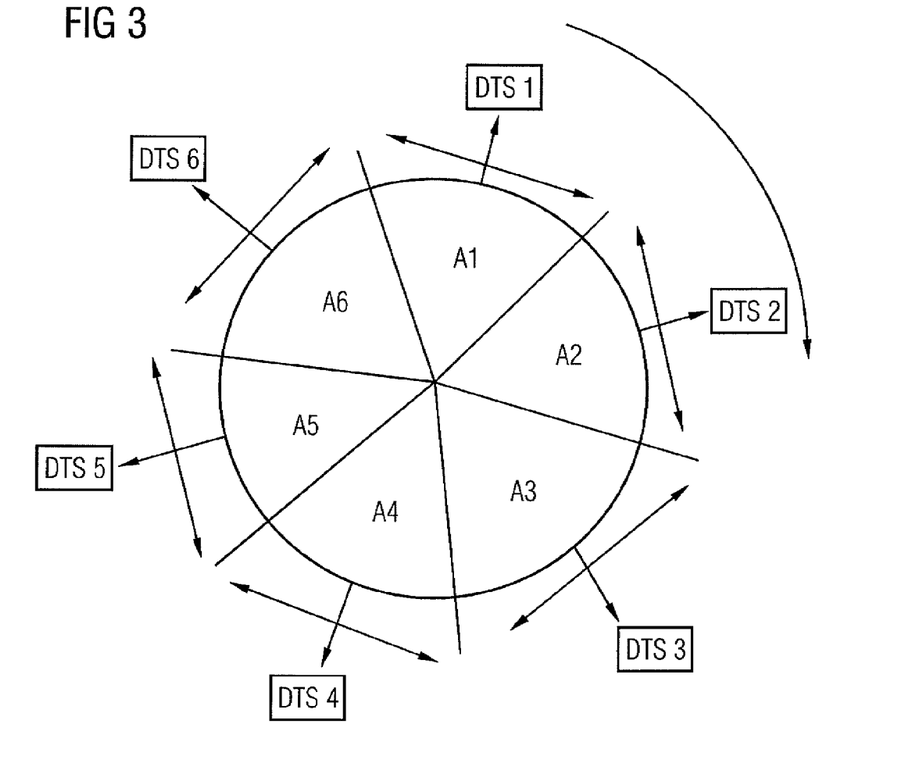
FIG. 3 shows a 360° rotation of an imaging device with a representation of angle ranges, within which travel takes place at different rotation speeds.

FIG. 3 shows the division of a complete 360° rotation of the imaging device 17, 19 into six different angle ranges that are assigned to the breathing phases shown in FIG. 2. The angle ranges assigned to breathing phases A1, A2, A4, and A5 are traveled through at a high rotation speed for the imaging device or gantry, whereas the angle ranges assigned to breathing phases A3 and A6 are traveled through at a slow rotation speed.

A first individual image DTS1 in the temporal series of the tomosynthesis images may be reconstructed from the raw image data recorded while the imaging device 17, 19 is rotating through angle range A1. The individual image DTS1 is assigned to the early inhalation phase.

A second individual image DTS2 in the temporal series of the tomosynthesis images may be reconstructed from the raw image data recorded while the gantry is rotating through angle range A2. The individual image DTS2 is assigned to the mid inhalation phase. This is continued in the other breathing phases analogously.

A temporal series of six tomosynthesis images DTSi (i=1 . . . 6) is obtained. The temporal series of tomosynthesis images is assigned to breathing phases Ai (i=1 . . . 6) described with the aid of FIG. 2. The imaging level of the six tomosynthesis images DTSi turns in keeping with the angle ranges, from which the raw image data for the respective tomosynthesis images DTSi was recorded.

If a maximum rotation speed of the CT gantry (or conebeam CT gantry) is one rotation in 6 s, then one breathing cycle may, as described above, be imaged in six phases. The six phases may be imaged with a better image quality if the rotation speed is less than 6 s (e.g., if the gantry is faster) because the motion-induced lack of sharpness may be reduced.

Figure 4:
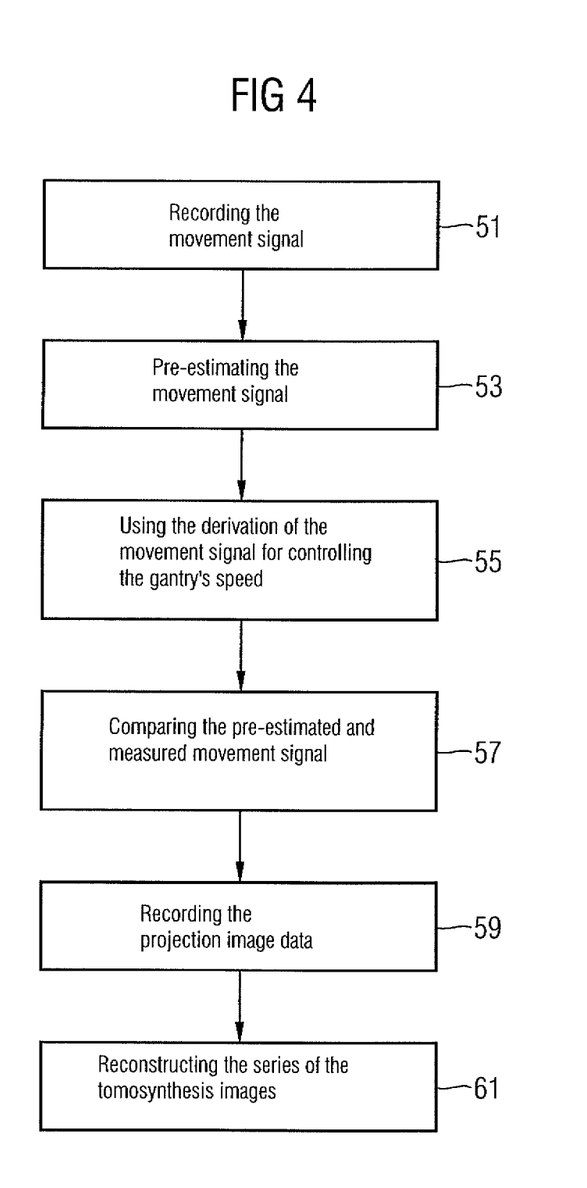
FIG. 4 is a flowchart illustrating one embodiment of a method applied to the imaging process.

FIG. 4 is a flowchart relating to a method showing how a motion speed of the imaging device may be controlled as a function of the motion speed of the object to be imaged.

This is based on knowing the movement signal of the breathing movement in advance. It may be assumed that the breathing signal is quasi time-invariant so long as a short period of one to two minutes is considered. Exceptions are irregularities caused by, for example, coughing and the like. The breathing signal may be predicted relatively reliably over a period of up to 1 s or even longer.

With the method described, a technique whereby the breathing signal is pre-estimated over a period of 0.5 to 1 s may be employed. The pre-estimated signal may be used for modeling the speed of the breathing movement so as to obtain an optimal sampling rate for the individual projection images, then forming the basis for reconstructing the breathing-resolved tomosynthesis.

For example, a support-vector regression, neuronal networks, polynomial methods, Kalman filters, or other algorithms may be used as the algorithm for the pre-estimation.

The breathing signal is recorded at a first act, for example, with the aid of optical surface or point scanners, with the aid of pressure belts (act 51).

The recorded breathing signal is used for producing a prediction model, using which the curve shape of the breathing signal over a short time period of, for example, 0.5 to 1 s may be predicted. The breathing cycle is pre-estimated with the aid of the prediction model (act 53).

The first derivation of the breathing signal in terms of time is formed, and the pre-estimated signal is used in that way to match the rotation speed of the gantry as a function of the first derivation such that the optimal sampling rate for breathing-resolved tomosynthesis imaging is set (act 55).

The current breathing signal continues being measured and compared with the pre-estimated signal (act 57). Recording of the image data may be terminated if a difference between the pre-estimated and measured signal exceeds a threshold. The gantry speed may also continue to be matched in order to compensate the difference.

The breathing-resolved projection image data is then recorded at the optimal sampling rate (act 59) and used to reconstruct the temporal series of the tomosynthesis images (act 61).

The method described is just an example. Various acts do not have to be implemented (e.g., pre-estimating of the breathing signal and making a comparison with the actually measured breathing signal may not be carried out). The rotation speed may be matched as a function of the measured or predicted breathing signal.

Figure 5:
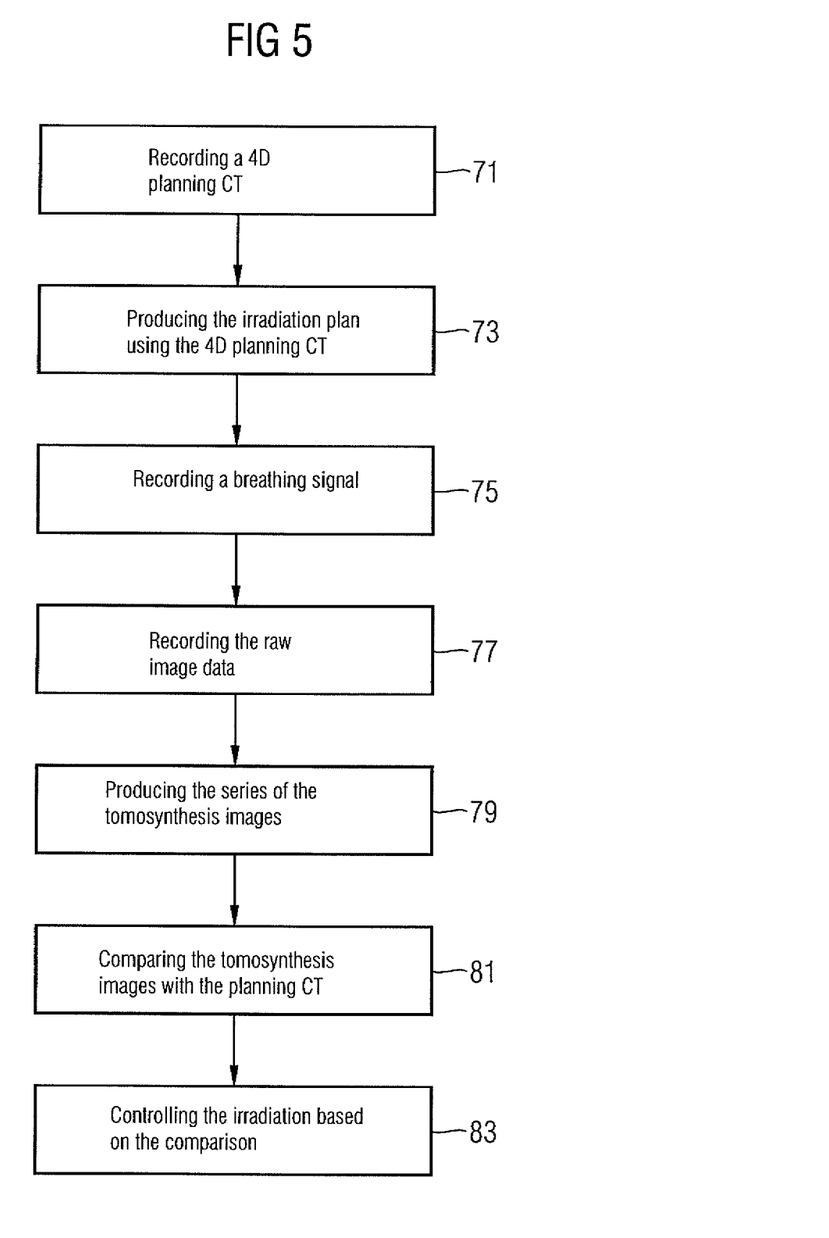
FIG. 5 is a flowchart illustrating one embodiment of a radiation-therapy method, for which the imaging method is used.

With the aid of the flowchart shown in FIG. 5, an example is explained of how the imaging method may be embedded in a flow within the scope of radiation therapy.

A four-dimensional planning CT is made at a first act (act 71).

Irradiating is planned using the 4DCT. Additional imaging modalities such as 4D magnetic resonance tomography or 4D positron-emission tomography may be employed if desired. The additional imaging modalities may be registered with the planning 4DCT. The phase angle of the four-dimensional data records may be taken account of (e.g., the phase of maximum exhalation in the CT relative to the phase of maximum exhalation in the MR will be registered). An irradiation plan is defined and optimized based on the 4DCT (e.g., and with the aid of the additional data records registered for the CT) (act 73).

The irradiation plan is conveyed to the radiation-therapy device, for example, directly or via an oncology information system (OIS).

A time-resolved image data record having at focus the target volume and surrounding organs at risk is recorded ahead of an irradiation session. An imaging method as described above is employed.

A surrogate signal for the breathing movement is recorded (act 75). The raw image data for the time-resolved tomosynthesis is recorded (act 77).

For that purpose, a CT synchronized with the breathing cycle is recorded with a slow rotation. The recording time for the raw image data corresponds roughly to the duration of the breathing phase (e.g., 4 to 6 s). The speed of the CT gantry is modulated during recording of the image data (e.g., as a function of the breathing signal) for recording the required angle range for each breathing phase.

A digital tomosynthesis is reconstructed for each breathing phase (act 79).

If, for example, a 360° rotation is executed in 6 s, six digital tomosynthesis volumes each imaging a breathing phase of 1 s duration may be reconstructed. The successive, cohesively recorded projection image data belonging to an assigned angle range is used for reconstructing an individual image.

The recorded four-dimensional digital tomosynthesis (e.g., the temporal series of the six individual images) may be correlated with the four-dimensional planning data records (act 81), and the information thereby obtained may be applied to controlling the irradiation (act 83).

An anatomical disparity between the planning data record and the data record recorded immediately before a treatment commences (e.g., the 4D digital tomosynthesis data record) may be compensated in various ways. For example, a geometric correction may be made where, for example, the target volume is repositioned by moving the patient, and a disparity is at least partially compensated thereby. A dosimetric correction is also possible, for example, by altering the original irradiation plan or even within the scope of completely recalculating the irradiation plan.

Alternatively or additionally, the external movement signal may be correlated with internal data about the location of the target volume (e.g., for controlling a tracking method).

Irradiating may be carried out, for example, in single or multiple fractions.

Acts 75 to 79 may be repeated in entirety during irradiating in order to check and, where necessary, adjust the radiation. Acts 75 to 79 may be performed within a narrower angle range, with tomosynthesis image data being recorded for, for example, only one to three breathing phases. That incomplete series of temporal tomosynthesis images may be used for checking the consistency of the location of the target volume and/or of the correlation of the location of the target volume with the external signal and, where applicable, matching the underlying model.

The target volume being represented tomographically in every breathing phase therefore offers an approach to implementing advanced 4D-IGRT strategies relatively easily such as, for example, a tracking method that uses an external signal's correlation with an internal image of the target volume. A gating method may be applied when the current three-dimensional location of the target volume is visualized before and/or during an irradiation session. The visualized current three-dimensional location of the target volume is used for controlling the gating method.

The described imaging method may be used for radiation-therapy applications. The described imaging method may also be useful for other applications such as, for example, c-arc-based interventional applications.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for time-resolved tomosynthesis imaging for a moving object, the method comprising:
    moving an imaging device comprising an x-ray source and an x-ray detector around the moving object and recording raw image data for a temporal series of tomosynthesis images, wherein the moving object is moving at a varying speed while the raw image data is being recorded;
    matching a motion speed of the imaging device to the varying speed of the moving object while the raw image data is being recorded; and
    reconstructing the temporal series of tomosynthesis images from the raw image data.

2. The method as claimed in claim 1, wherein moving the imaging device comprises moving the imaging device around the moving object such that the motion of the x-ray source and the x-ray detector is in a single plane.

3. The method as claimed in claim 2, wherein the imaging device is moved around the moving object through 360°.

4. The method as claimed in claim 1, wherein moving the imaging device comprises moving the imaging device such that an angle range, from which the raw image data for reconstructing an individual image in the temporal series of tomosynthesis images is recorded, is covered in less than 2 seconds.

5. The method as claimed in claim 4, wherein the angle range is covered in less than 1.5 seconds.

6. The method as claimed in claim 5, wherein the angle range is covered in less than 1 second.

7. The method as claimed in claim 4, wherein the angle range, from which the raw image data for reconstructing the individual image in the temporal series of tomosynthesis images is recorded, is 35° to 100°.

8. The method as claimed in claim 7, wherein the angle range is 40° to 70°.

9. The method as claimed in claim 1, wherein moving the imaging device comprises moving the imaging device long enough for at least four phases of movement of the moving object to be imaged in the temporal series of the tomosynthesis images.

10. The method as claimed in claim 9, wherein moving the imaging device comprises moving the imaging device long enough for at least six phases of movement of the moving object to be imaged in the temporal series of the tomosynthesis images.

11. The method as claimed in claim 1, further comprising using the temporal series of the tomosynthesis images in preparation for a radiation-therapy session, during the radiation-therapy session, or in preparation for the radiation-therapy session and during the radiation-therapy session.

12. The method of claim 1, further comprising:
    identifying an estimated movement signal for the moving object;
    determining an actual movement signal for the moving object;
    comparing the estimated movement signal to the actual movement signal; and
    terminating the recording of the raw image data based on the comparing.

13. The method of claim 12, wherein the comparing comprises determining a difference between the estimated movement signal and the actual movement signal, and
    wherein the recording of the raw image data is terminated when the determined difference is greater than a predetermined threshold.

14. The method of claim 1, wherein matching the motion speed of the imaging device to the varying speed of the moving object comprises:
    determining steepness of a surrogate signal characterizing motion of the moving object; and changing the motion speed of the imaging device based on the determined steepness of the surrogate signal characterizing the motion of the moving object.

15. The method of claim 14, wherein the surrogate signal comprises a first portion and a second portion, the first portion of the surrogate signal having a greater steepness than the second portion of the surrogate signal, and
wherein the motion speed of the imaging device corresponding to the second portion of the surrogate signal is less than the motion speed of the imaging device corresponding to the first portion of the surrogate signal.

16. The method as claimed in claim 1, wherein reconstruction planes of two successive individual images in the temporal series of the tomosynthesis images are at an angle of at least 30° relative to each other.

17. The method as claimed in claim 16, wherein the angle is at least 40°.

18. The method as claimed in claim 17, wherein the angle is at least 50°.

19. The method as claimed in claim 16, wherein moving the imaging device comprises moving the imaging device such that the motion of the x-ray detector and x-ray source is in a single plane.

20. An imaging device comprising:
an x-ray source and an x-ray detector;
a control device configured to:
  control movement of the x-ray source and the x-ray detector; and
  control the x-ray source and x-ray detector for recording raw image data of a moving object; and
a reconstruction device configured to reconstruct a temporal series of tomosynthesis images from the raw image data,
wherein the control device is configured to match a motion speed of the imaging device, while the raw image data is being recorded, to a varying speed, at which the moving object is moving.

21. The imaging device as claimed in claim 20, wherein the imaging device is integrated in a radiation-therapy device such that a therapeutic radiation source is also moved when the imaging device is moved.

* * * * *